United States Patent [19]

Reuter et al.

[11] 4,282,116

[45] Aug. 4, 1981

[54] SUPPORTED CATALYST CONTAINING VANADIUM AND TITANIUM AND/OR ZIRCONIUM FOR THE PREPARATION OF PHTHALIC ANHYDRIDE

[75] Inventors: Peter Reuter, Bad Durkheim; Kurt Blechschmitt, Schifferstadt; Friedrich Wirth, Ludwigshafen, all of Fed. Rep. of Germany

[73] Assignee: BASF Aktiengesellschaft, Fed. Rep. of Germany

[21] Appl. No.: 138,413

[22] Filed: Apr. 8, 1980

[30] Foreign Application Priority Data

Apr. 11, 1979 [DE] Fed. Rep. of Germany ....... 2914683

[51] Int. Cl.$^3$ ...................... B01J 21/06; B01J 23/22; B01J 35/00
[52] U.S. Cl. .............................. 252/461; 252/477 R; 260/346.4
[58] Field of Search ........................... 252/461, 477 R

[56] References Cited

U.S. PATENT DOCUMENTS

| 3,464,930 | 9/1969 | Friedrichsen et al. .............. 252/469 |
| 3,565,829 | 2/1971 | Friedrichsen et al. .............. 252/464 |
| 4,002,653 | 1/1977 | Reuter et al. .................... 252/461 X |
| 4,036,783 | 7/1977 | Blechschmitt et al. ............. 252/461 |

*Primary Examiner*—W. J. Shine
*Attorney, Agent, or Firm*—Keil & Witherspoon

[57] ABSTRACT

A supported catalyst, containing vanadium and titanium and/or zirconium, obtained by applying a mixture of finely divided titanium dioxide and/or zirconium dioxide, and a solution or suspension of a vanadium compound, to an inert, non-porous, ring-shaped carrier having an external diameter of from 6 to 10 mm, a length of from 4 to 10 mm and a wall thickness of from 0.5 to 3 mm, the two end faces of the ring-shaped carrier being outwardly beveled at an angle such that the length of the outer cylindrical wall is at least 20% shorter than the length of the inner cylindrical wall.

2 Claims, 3 Drawing Figures

SUPPORTED CATALYST CONTAINING VANADIUM AND TITANIUM AND/OR ZIRCONIUM FOR THE PREPARATION OF PHTHALIC ANHYDRIDE

The present invention relates to a novel supported catalyst containing vanadium and titanium and/or zirconium, and to its use for the preparation of phthalic anhydride by catalytic oxidation of o-xylene or naphthalene.

Supported catalysts containing vanadium and titanium and/or zirconium, as described, for example, in German Pat. No. 1,442,590, German Laid-Open Application DOS No. 1,642,938 or German Published Application DAS No. 2,510,994, have already been proposed for the preparation of phthalic anhydride (hereafter referred to as PA) by catalytic oxidation of o-xylene or naphthalene with air or with an oxygen-containing gas. These catalysts are prepared by applying a mixture, containing titanium dioxide and/or zirconium dioxide and a vanadium compound, to a carrier which is, for example, in the shape of spheres, pills, cones or rings, in such a way that after drying the carrier possesses a coating, from about 0.02 to 2 mm thick, of the active material comprising vanadium pentoxide and titanium dioxide and/or zirconium dioxide.

Spherical catalysts, and in particular the ring-shaped catalysts described in German Published Application DAS No. 2,510,996, have proved very useful.

In the continuous preparation of PA, it is desirable to keep the salt bath temperature as low as possible, so as to protect the catalyst. For economic reasons, a high throughput over the catalyst is also desirable.

Limits are imposed on these endeavors by the fact that, for example, the content of phthalide in the PA produced increases at lower temperatures and higher throughputs. Since the phthalide content is a measure of the quality of the PA, the formation of phthalide must be suppressed as far as possible. It is an object of the present invention to provide a catalyst which when used, for example, for the preparation of PA by oxidizing o-xylene or napthalene, gives a PA of high quality at relatively low salt bath temperatures and relatively high throughput.

We have found that this object is achieved and that a supported catalyst, containing vanadium and titanium and/or zirconium, which is obtained by applying a mixture of finely divided titanium dioxide and/or zirconium dioxide and a solution or suspension of a vanadium compound to an inert, non-porous, ring-shaped carrier having an outer diameter of from 6 to 10 mm, a length of from 4 to 10 mm and a wall thickness of from 0.5 to 3 mm, and in which the carrier, after drying, carries a coating, from 0.05 to 1 mm thick, of an active material containing from 1 to 30 percent by weight of vanadium pentoxide and from 70 to 99% by weight of titanium dioxide and/or zirconium dioxide, possesses the desired properties if the ring-shaped carrier is beveled outward on both end faces at an angle such that the length of the outer cylindrical wall is at least 20% shorter than the length of the inner cylindrical wall.

This novel catalyst offers surprising advantages, for example when preparing PA from o-xylene or naphthalene, in respect of the life of the catalyst and the achievable throughput.

The novel catalyst is based on ring-shaped carriers having an outer diameter of from 6 to 10 mm, advantageously from 7.3 to 8.6 mm, a length of from 4 to 10 mm, advantageously from 5.3 to 7.0 mm, and a wall thickness of from 0.5 to 3 mm, advantageously from 0.5 to 2 mm. The essential feature of the novel ring-shaped catalyst is that the two round end faces of the ring-shaped carrier are beveled outward at an angle such that the length of the outer cylindrical wall is at least 20%, preferably at least 50%, shorter than the length of the inner cylindrical wall. The beveled end faces can be plane but are advantageously convex. The length of the outer cylindrical wall is shortened relative to the inner cylindrical wall, which is not affected by the beveling. The length of this outer cylindrical wall (1a) is, for example, from 0 to 8 mm, advantageously from 0.2 to 5 mm.

BRIEF DESCRIPTION OF THE DRAWINGS

In the drawings, suitable shapes for the novel catalyst are shown in side views in FIGS. 1 and 3 and a top view of FIG. 2.

The rings consist of inert, non-porous materials, such as iron, steel, aluminum, procelain, alumina or silicates, e.g. magnesium silicate, aluminum silicate or zirconium silicate.

Figure 1:
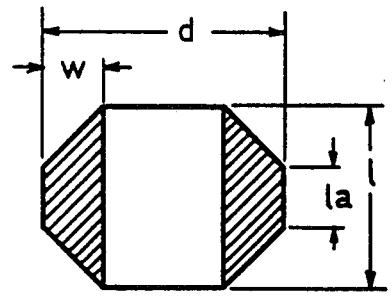
Figure 2:
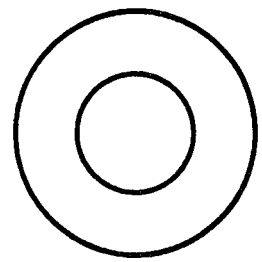
Figure 3:
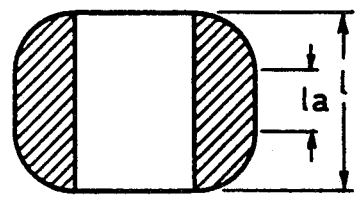

The carrier is coated with the catalytic material by applying a mixture of finely divided titanium dioxide and/or zirconium dioxide and a solution or suspension of a vanadium compound to the carrier. The finely divided titanium dioxide used is advantageously anatase having a specific inner surface area of from 5 to 20 $m^2/g$.

Suitable vanadium compounds are vanadium pentoxide and vanadium compounds which at a higher temperature are converted to vanadium pentoxide, for example vanadyl oxalate, vanadyl formate, vanadyl tartrate and ammonium vanadate. Coprecipitates of titanium dioxide and vanadium pentoxide, or titanium-vanadium compounds, for example titanium vanadates, may also be employed. The mixture to be applied to the carrier is prepared in a conventional manner, for example by mixing the finely divided titanium dioxide and/or zirconium dioxide with the solution or suspension of the vanadium compound in water and/or in an organic solvent, such as formamide or ethanolamine.

The coating operation itself is advantageously carried out by applying the mixture, containing the catalytic substances, to the carrier which has been heated to, for example, from 110° to 500° C. In the finished catalyst, the active material accounts, for example, for from 4 to 30% by weight of the catalyst. The thickness of the coating of active material is preferably from 0.05 to 0.5 mm.

The mixture, containing the catalytic substances, is formulated so that after drying the active material present on the carrier contains from 1 to 30, preferably from 1 to 15,% by weight of vanadium pentoxide and/or zirconium oxide. The catalytic material can, for example, additionally contain up to 5% of other substances, such as oxides of the elements rubidium, cesium, phosphorus or antimony. In such cases, appropriate amounts of the said oxides, or of compounds which on coating and heating are converted to these oxides, are added to the mixture which is to be applied to the carrier.

The novel catalysts may be used, for example, to prepare phthalic anhydride by oxidizing o-xylene or naphthalene, to prepare maleic anhydride by oxidizing benzene or unsaturated aliphatic $C_4$-hydrocarbons, to prepare pyromellitic anhydride by oxidizing durene or other 1,2,4,5-tetraalkylbenzenes, to prepare naphthalic acid from acenaphthene, to prepare quinones by oxidizing naphthalene to naphthoquinone or by oxidizing anthracene, substituted indans or diphenylmethane compounds, eg. 2-methyldiphenylmethane, to anthraquinone, by means of air or an oxygen-containing gas. Particularly advantageous results are obtained in the catalytic oxidation of o-xylene or naphthalene to PA by means of air. The oxidation is advantageously carried out in a conventional manner in tubular reactors with salt bath cooling, at salt bath temperatures of from 330° to 450° C., preferably from 340° to 400° C. The novel catalysts can be subjected to throughputs of from 4 to 10 cubic meters (S.T.P.) of air or of oxygen-containing carrier gas per hour per tube (the tube diameter being from about 16 to 40 mm and the tube length from about 1 to 4 m). The air or gas can be charged with from 20 to 100 g of o-xylene or naphthalene per cubic meter (S.T.P.).

Surprisingly, it has been found that when using the catalysts according to the invention, the oxidation of o-xylene or napthalene gives a PA of substantially better quality than is obtained with conventional catalysts under identical experimental conditions. Since the PA obtained with the catalysts according to the invention has a lower phthalide content, it is possible to operate the novel catalysts at lower salt bath temperatures and to keep them longer at low temperatures. Accordingly, the temperature increases which become necessary with gradual aging of the catalyst can be made at longer intervals of time than with the conventional catalysts. Both factors lead, as experience has shown, to a longer catalyst life and to a higher total yield over the life of the catalyst.

Instead of lowering the salt bath temperature it is also possible, when using the catalysts according to the invention, to increase the throughput of air or oxygen-containing carrier gas compared to that used with conventional catalysts. It is also possible to charge the air or the oxygen-containing carrier gas with more o-xylene or naphthalene per unit volume of air or carrier gas than in the case of the conventional ring-shaped catalysts, without a drop in the quality of the resulting PA. This allows a saving of energy in the preparation of PA.

A comparison with conventional supported catalysts shows the greater effectiveness of the novel catalysts. If the catalysts according to the invention and the ring-shaped catalyst disclosed in German Published Application DAS No. 2,510,996 are employed at the same salt bath temperature for the oxidation of o-xylene, a PA having the same low phthalide content is obtained if, using an air stream of 4 cubic meters (S.T.P.)/h per liter of catalyst, the o-xylene content of 62 g/cubic meter (S.T.P.) of air, used with the conventional catalyst, is increased to 85 g/cubic meter (S.T.P.) of air when using the catalyst according to the invention, or if, for the same content of 62 g of o-xylene/cubic meter (S.T.P.) of air, the air stream is increased, in the case of the catalyst according to the invention, to 5.5 cubic meters (S.T.P.)/h per liter of catalyst.

EXAMPLE 1

1,000 g of steatite rings having an external diameter (d) of 8 mm, a length (l) of 6 mm and a wall thickness (w) of 1.5 mm, and having their end faces peripherally beveled outward so that the length of the outer cylindrical wall (1a) is 2.0 mm, are heated in a coating drum at 260° C. At this temperature, suspension comprising 400 g of anatase having an inner surface area of 11.2 m$^2$/g, 73.6 g of vanadyl oxalate (corresponding to 30.1 g of vanadium pentoxide), 500 g of water and 100 g of formamide is sprayed onto the rings until the weight of the active material applied is 12.0% of the total weight of catalyst.

The catalytic material consists of 7.0% by weight of vanadium pentoxide and 93.0% by weight of titanium dioxide. The average thickness of the coating is 0.13 mm.

1,150 g of the catalyst prepared in this way are introduced into a vertical iron tube of 25 mm internal diameter and 3 m length, the tube being surrounded by a salt bath to regulate its temperature. 230 g of o-xylene mixed with 5,500 liters of air at 370° C. are passed, per hour, over this catalyst bed.

PA is obtained in a yield of 115% by weight, based on 100% pure o-xylene; the product contains 0.012% by weight of phthalide.

COMPARATIVE EXAMPLE

If instead of the rings described in Example 1, steatite rings having an external diameter of 8 mm, a length of 6 mm, a wall thickness of 1.5 mm and parallel end faces instead of beveled end faces are used, and in other respects the procedure described in the Example is followed, PA is obtained in a yield of 114.5% by weight, based on 100% pure o-xylene; the product contains 0.035% by weight of phthalide. To lower the phthalide content in the PA to 0.012% by weight, the hourly throughput must be reduced to 184 g of o-xylene mixed with 4,500 liters of air.

EXAMPLE 2

(a) Preparation of the catalyst I 600 g of steatite rings having an external diameter (d) of 8 mm, a length (l) of 6 mm and a wall thickness (w) of 1.5 mm, and having end faces beveled outward so that the length of the outer cylindrical wall (1a) is 2 mm, are heated at 260° C. in a coating drum and sprayed with a suspension, consisting of 400 g of anatase having an inner surface area of 11 m$^2$/g, 73.2 g of vanadyl oxalate (vanadium content corresponding to 41% of V$_2$O$_5$), 500 g of water, 100 g of formamide and 1.09 g of rubidium carbonate, until the weight of the catalytic material applied is 10% of the total catalyst weight. The catalytic material thus applied consists of 0.202% by weight of rubidium oxide (corresponding to 0.186% by weight of rubidium), 70% by weight of vanadium pentoxide and 92.84% by weight of titanium dioxide, so that there is 1 atom of rubidium per 35.3 atoms of vanadium. The rubidium content, based on anatase, is 0.20%.

(b) Preparation of catalyst II

The procedure described under a is followed, but instead of rubidium carbonate 4.87 g of ammonium hydrogen phosphate are added. The weight of the applied catalytic material amounts to 10% of the total weight of the finished catalyst. The catalyst layer consists of 0.3% by weight of phosphorus, 7.0% by weight of vanadium pentoxide and 92.7% by weight of titanium dioxide.

(c) Use of the catalysts 1.60 m of catalyst II, followed by 1.20 m of catalyst I, are introduced into a 3.25 m long iron tube of internal diameter 25 mm. The iron tube is surrounded by a salt melt to regulate its temperature. Per hour, 382 g of o-xylene mixed with 4,500 liters of air, at 363° C., are passed downward through the tube.

PA is obtained in a yield of 114.1% by weight, based on 100% pure o-xylene; the product contains 0.015% by weight of phthalide.

COMPARATIVE EXAMPLE

If instead of the rings described in Example 1, steatite rings having an external diameter of 8 mm, a length of 6 mm, a wall thickness of 1.5 mm and parallel end faces instead of beveled end faces are used, and in other respects the procedure described in Example 2 is followed, PA is obtained in a yield of 114% by weight, based on 100% pure o-xylene; the product contains 0.081% by weight of phthalide. To lower the phthalide content in the PA to 0.015% by weight, the hourly throughput must be reduced to 292 g of o-xylene mixed with 4,500 liters of air.

EXAMPLE 3

1,000 g of steatite rings having an external diameter (d) of 8 mm, a length (l) of 6 mm and a wall thickness (w) of 1.5 mm, and having end faces beveled outward so that the length of the outer cylindrical wall (1a) is 2 mm, are heated at 260° C. in a coating drum and sprayed with the suspension described in Example 1, until the weight of active material applied is 8.0% of the total weight of the catalyst.

The catalyst material consists of 7.0% by weight of vanadium pentoxide and 93.0% by weight of titanium dioxide. The average coating thickness is 0.09 mm.

1,130 g of the catalyst prepared as above are introduced into a vertical iron tube of 25 mm internal diameter and 3 m length, the tube being surrounded by a salt bath to regulate its temperature. Per hour, 160 g of naphthalene together with 4,000 liters of air at 372° C. are passed over this catalyst bed.

The yield achieved is 103.5% by weight, based on 100% pure naphthalene. The naphthoquinone content of the PA obtained is 0.3% by weight.

COMPARATIVE EXAMPLE

If instead of the catalyst rings described in Example 3, the corresponding steatite rings with nonbeveled end faces are used, a PA containing 0.8% by weight of naphthoquinone is obtained under the experimental conditions described in Example 3. To reduce the naphthoquinone content to 0.3%, the salt bath temperature must be raised by 10° C. to 382° C.

We claim:

1. A supported catalyst containing vanadium and titanium and/or zirconium, obtained by applying a mixture of finely divided titanium dioxide and/or zirconium dioxide and a solution or suspension of a vanadium compound to an inert, non-porous, ring-shaped carrier having an external diameter of from 6 to 10 mm, a length of from 4 to 10 mm and a wall thickness of from 0.5 to 3 mm in such a way that the carrier, after drying, carries a coating from 0.05 to 1 mm thick of an active material containing from 1 to 30% by weight of vanadium pentoxide and from 70 to 99% by weight of titanium dioxide and/or zirconium dioxide, wherein the two end faces of the ring-shaped carrier are outwardly beveled at an angle such that the length of the outer cylindrical wall is at least 20% shorter than the length of the inner cylindrical wall.

2. A supported catalyst as claimed in claim 1, wherein the beveled end faces of the ring-shaped carrier are convex.

* * * * *